United States Patent [19]

Haas et al.

[11] Patent Number: 5,508,420

[45] Date of Patent: Apr. 16, 1996

[54] PROCESS AND INTERMEDIATES FOR THE PREPARATION OF TRIAZOLINONES

[75] Inventors: Wilhelm Haas, Pulheim; Karl-Heinz Linker; Kurt Findeisen, both of Leverkusen, all of Germany

[73] Assignee: Bayer Aktiengesellschaft, Leverkusen, Germany

[21] Appl. No.: 347,985

[22] Filed: Dec. 5, 1994

[30] Foreign Application Priority Data

Dec. 10, 1993 [DE] Germany ............... 43 42 190.3

[51] Int. Cl.⁶ .................. C07D 249/12; C07D 249/14
[52] U.S. Cl. ................... 548/263.2; 548/263.8; 548/264.6
[58] Field of Search .............. 548/263.2, 263.8, 548/264.6

[56] References Cited

U.S. PATENT DOCUMENTS 3,780,052  12/1973  Cebalo et al. .

OTHER PUBLICATIONS

G. Mazzon, et al. Il Farmaco, Edizione Scientifica, vol. 36, No. 3 pp. 181–196 (1981) "Comprehensive Heterocyclic Chemistry," A. Katrilzky et al, vol. 5, part 4A, pp. 758 and 759 Pergamon Press (1981).

C. Temple, Jr., "The Chemistry of Heterocyclic Compounds (WeissBerger) (1981) Triazoles 1,2,4", J. Montegomery, ed, pp. 261, 262, 286 & 287, John Wiley & Son, NY.

M. Y. Mhasalkar et al. J. Med. Chem., vol. 14, No. 3, pp. 260–266 (1971).

Blackman et al, "Triazoles. Part XI. Synthesis, etc." J. Chem Soc C. (c), 1970, 17, pp. 2403–2409.

Landquist et al, "Oxidative Cyclisation, etc" J. Chem C., 1970, 1, pp. 63–66.

Vlasova et al, "Reaction of Ethylene Oxide, etc" CA–76: 126876c (1972).

*Primary Examiner*—Patricia L. Morris
*Attorney, Agent, or Firm*—Sprung Horn Kramer & Woods

[57] ABSTRACT

The invention relates to a new process and to new intermediates for the preparation of triazolinones, most of which are known, of the general formula (I)

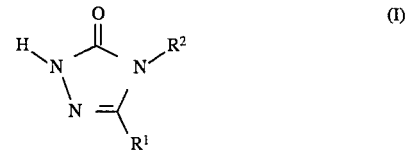

in which

R¹ and R² have the meanings given in the application, and which can be used as intermediates for the preparation of herbicides and insecticides.

5 Claims, No Drawings

PROCESS AND INTERMEDIATES FOR THE PREPARATION OF TRIAZOLINONES

The invention relates to a new process and to new intermediates for the preparation of triazolinones, most of which are known and which can be used as intermediates for the preparation of herbicides and insecticides.

It has been disclosed that certain substituted triazolinones, such as, for example, the compound 4-methyl- 5-trifluoromethyl-2,4-dihydro-3H-1,2,4-triazol-3-one, are obtained when corresponding triazolinethiones, such as, for example, the compound 4-methyl-5-trifluoromethyl- 2,4-dihydro-3H-1,2,4-triazole-3-thione, are first reacted with an alkylating agent, such as, for example, methyl iodide, in the presence of an acid-binding agent such as, for example, sodium methylate, the resulting alkylthiotriazole derivative is isolated in the customary manner, then heated together with hydrogen peroxide in the presence of acetic acid, neutralized when cold and worked up in the customary manner (cf. U.S. Pat. No. 3,780,052—Example 2).

It has also been disclosed that the abovementioned compound 4-methyl-5-trifluoromethyl-2,4-dihydro-3H- 1,2, 4-triazol-3-one can also be obtained by heating 1-trifluoroacetyl-4-methyl-semicarbazide at 160° C. to 180° C. followed by extraction with ethyl acetate and column chromatography (cf. U.S. Pat. No. 3,780,052— Example 3).

However, yield and quality of the products obtained using the two synthesis methods indicated are highly unsatisfactory.

The present application relates to a new process for the preparation of triazolinones of the general formula (I)

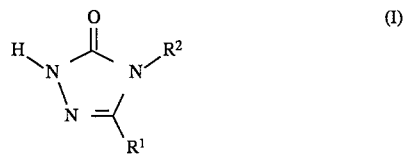

in which
R$^1$ represents an in each case optionally substituted radical from the series comprising alkyl or cycloalkyl and
R$^2$ represents amino or an in each case optionally substituted radical from the series comprising alkyl, alkenyl, alkinyl, alkoxy, alkylamino, dialkylamino, cycloalkyl, cycloalkylalkyl or phenyl,
characterized in that triazolinethiones of the general formula (II)

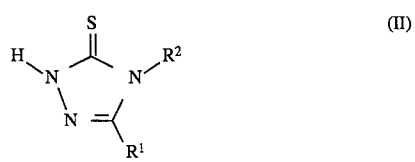

in which
R$^1$ and R$^2$ have the abovementioned meanings,
are reacted with an oxidant, if appropriate in the presence of a reaction auxiliary and if appropriate in the presence of a diluent, at temperatures between 0° C. and 100° C.,
and the synthesized triazolesulphonic acids or the salts thereof of the general formula (III)

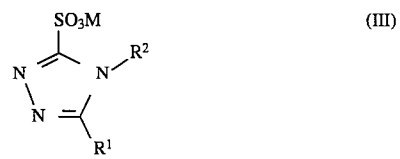

in which
R$^1$ and R$^2$ have the abovementioned meanings and
M represents hydrogen or a metal equivalent,
which have been obtained here ("in the first step of the process according to the invention") are reacted with water, if appropriate in the presence of an acid, at temperatures between 20° C. and 120° C., if appropriate after an intermediate isolation step ("in the second step of the process according to the invention").

Surprisingly, the process according to the invention allows the triazolinones of the general formula (I) to be obtained in a simple manner in high yields, which are considerably improved compared with the prior art, and in high purity.

The process according to the invention therefore represents a valuable enrichment of the prior art.

Compounds of the formula (I) which are prepared by the process according to the invention are preferably those in which
R$^1$ represents alkyl having 1 to 6 carbon atoms which is optionally substituted by halogen, cyano or C$_1$–C$_4$-alkoxy, or represents cycloalkyl having 3 to 6 carbon atoms which is optionally substituted by halogen, cyano or C$_1$–C$_4$-alkyl, and
R$^2$ represents amino, a radical from the series comprising alkyl, alkenyl, alkinyl, alkoxy, alkylamino or dialkylamino, each of which has up to 6 carbon atoms in the alkyl, alkenyl or alkinyl groups and each of which is optionally substituted by halogen, cyano or C$_1$–C$_4$-alkoxy, or represents a radical from the series comprising C$_3$–C$_6$-cycloalkyl, C$_3$–C$_6$-cycloalkyl-C$_1$–C$_2$-alkyl or phenyl, each of which is optionally substituted by halogen, cyano, C$_1$–C$_4$-alkyl, C$_1$–C$_4$-alkoxy or C$_1$–C$_4$-alkoxycarbonyl.

The hydrocarbon radicals mentioned in the definitions of the radicals, such as alkyl, also in combinations with hetero atoms, such as in alkoxy, alkylthio or alkylamino, are straight-chain or branched even where this is not expressly stated.

Halogen generally represents fluorine, chlorine, bromine or iodine, preferably fluorine, chlorine or bromine, in particular fluorine or chlorine.

Compounds of the formula (I) which are prepared by the process according to the invention are particularly those in which
R$^1$ represents methyl, ethyl, n- or i-propyl, or n-, i- or s-butyl, each of which is optionally substituted by fluorine, chlorine, bromine, cyano, methoxy or ethoxy, or represents cyclopropyl, cyclopropylmethyl, cyclobutyl, cyclopentyl or cyclohexyl, each of which is optionally substituted by fluorine, chlorine, bromine, cyano or methyl, and
R$^2$ represents amino, a radical from the series comprising methyl, ethyl, n- or i-propyl, n-, i- or s-butyl, allyl, propargyl, methoxy, ethoxy, n- or i-propoxy, n-, i- or s-butoxy, methylamino, ethylamino, n- or i-propylamino, n-, i- or s-butylamino, dimethylamino or diethylamino, each of which is optionally substituted by fluorine, chlorine, cyano, methoxy or ethoxy, or represents a radical from the series comprising cyclopropyl, cyclobutyl, cyclopentyl or cyclohexyl or phenyl, each of which is optionally substituted by fluorine, chlorine, bromine, cyano, methyl, ethyl, n- or i-propyl, methoxycarbonyl or ethoxycarbonyl.

A very particularly preferred group of compounds which can be prepared by the process according to the invention are those compounds of the formula (I) in which $R^1$ represents methyl, ethyl, n- or i-propyl, cyclopropyl or cyclopropylmethyl, each of which is mono-, di-, tri-, tetra-, penta-, hexa- or hepta-substituted by fluorine and/or chlorine and $R^2$ represents methyl, ethyl, n- or i-propyl, methoxy, ethoxy, methylamino, ethylamino, dimethylamino, cyclopropyl, phenyl or tolyl.

The definitions of radicals which have been mentioned above in general or in preferred ranges apply both to the end products of the formula (I) and, analogously, to the starting substances or intermediates required in each case for their preparation.

These definitions of radicals can be combined with each other as desired, that is to say combinations between ranges of preferred compounds which have been indicated are also possible.

If, for example, 5-difluoromethyl-4-methoxy-2,4-dihydro- 3H-1,2,4-triazole-3-thione and hydrogen peroxide are used as starting substances, the course of the reaction in the process according to the invention can be outlined by the following equation:

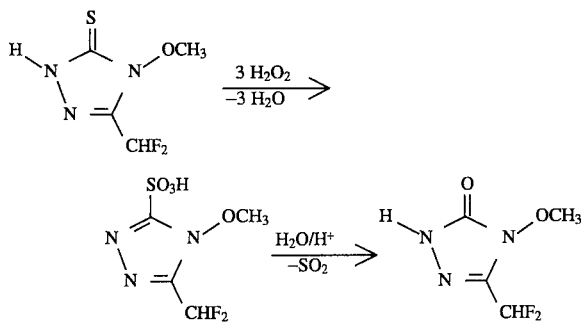

Formula (II) provides a general definition of the triazolinethiones to be used as starting substances in the process according to the invention for the preparation of the compounds of the general formula (I). In formula (II), $R^1$ and $R^2$ preferably, or in particular, have the meaning Which has already been indicated above in connection with the description of the compounds of the formula (I) as being preferred, or particularly preferred, for $R^1$ and $R^2$.

The triazolinethiones of the general formula (II) are known and/or can be prepared by processes known per se (cf. U.S. Pat. No. 3,719,686 and U.S. Pat. No. 3,780,052).

The triazolinethiones of the general formula (II) are obtained when carboxylic acids of the general formula (IV)

$$R^1\text{---CO---X} \qquad (IV)$$

in which $R^1$ has the abovementioned meaning and

X represents hydroxyl or halogen are reacted with alkylthiosemicarbazides of the general formula (V)

$$R^2\text{---NH---CS---NH---NH}_2 \qquad (V)$$

in which $R^2$ has the abovementioned meaning at temperatures between 0° C. and 100° C. (cf. the Preparation Examples).

The triazolesulphonic acids and the salts thereof of the general formula (III), which are synthesized as intermediates while carrying out the process according to the invention, are as yet not known from the literature; as new substances, they are part of the present application.

In formula (III), $R^1$ and $R^2$ preferably, or in particular, have the meaning which has already been mentioned above in connection with the description of the compounds of the formula (I) as being preferred, or particularly preferred, for $R^1$ and $R^2$; M preferably represents an alkali metal equivalent or an alkaline earth metal equivalent, in particular sodium or potassium.

The process according to the invention is carried out using an oxidant. Examples of suitable oxidants are oxygen, ozone, hydrogen peroxide, chlorine, sodium hypochlorite solution, sodium permanganate, potassium permanganate, nitric acid, sodium dichromate, potassium dichromate, sodium peroxodisulphate, potassium peroxodisulphate, sodium perborate, potassium perborate, performic acid, peracetic acid, perpropionic acid and optionally halogenated perbenzoic acids. Hydrogen peroxide is particularly preferred as oxidant in this case.

Suitable reaction auxiliaries—in particular when hydrogen peroxide is used—are, especially, salts of metals of groups IVb, Vb and VIb of the Periodic Table of the Elements. Examples which may be mentioned are sodium (meta)vanadate, sodium molybdate and sodium tungstate.

Other suitable reaction auxiliaries are the chemicals which are usually used as acid acceptors. Suitable acid acceptors are all customary inorganic or organic bases. These include, for example, the hydroxides, alcoholates, acetates, carbonates or hydrogen carbonates of alkaline earth metals or alkali metals, such as, for example, sodium hydroxide, potassium hydroxide, sodium methylate, sodium ethylate, potassium tert-butylate, sodium acetate, potassium acetate, calcium acetate, sodium carbonate, potassium carbonate, potassium hydrogen carbonate or sodium hydrogen carbonate. Reaction auxiliaries which are particularly preferred in the first step of the process according to the invention are sodium hydroxide and potassium hydroxide.

The process according to the invention is preferably carried out using a diluent. Suitable diluents are, in particular, aliphatic, alicyclic or aromatic, optionally halogenated hydrocarbons, such as, for example, benzine, benzene, toluene, xylene, chlorobenzene, dichlorobenzene, petroleum ether, hexane, cyclohexane, dichloromethane, chloroform, tetrachloromethane; ethers, such as diethyl ether, diisopropyl ether, dioxane, tetrahydrofuran or ethylene glycol dimethyl ether or ethylene glycol diethyl ether; ketones, such as acetone, butanone or methyl isobutyl ketone; nitriles, such as acetonitrile, propionitrile or benzonitrile; amides, such as N,N-dimethylformamide, N,N-dimethylacetamide, N-methyl-formanilide, N-methyl-pyrrolidone or hexamethylphosphoric triamide; carboxylic acids, such as formic acid, acetic acid or propionic acid, esters, such as methyl acetate or ethyl acetate, sulphoxides, such as dimethyl sulphoxide, alcohols, such as methanol, ethanol, n- or i-propanol, ethylene glycol monomethyl ether, ethylene glycol monoethyl ether, diethylene glycol monomethyl ether, diethylene glycol monoethyl ether, their mixtures with water, or pure water.

Water is particularly preferred as diluent in the first step of the process according to the invention.

When carrying out the first step of the process according to the invention, the reaction temperatures can be varied in a substantial range. In general, the process is carried out at temperatures between 0° C. and 100° C., preferably at temperatures between 20° C. and 80° C., in particular at temperatures between 30° C. and 60° C.

The process according to the invention is generally carried out under atmospheric pressure. However, it can also be carried out under elevated or reduced pressure, in general between 0.1 bar and 10 bar.

To carry out the first step of the process according to the invention, between 3 and 4 mole, preferably between 3.0 and 3.5 mole equivalents, of an oxidant are generally employed per mole of triazolinethione of the formula (II).

If appropriate, the second step of the process according to the invention is carried out in the presence of an acid. Inorganic or organic protonic acids, such as, for example, hydrochloric acid, sulphuric acid, methanesulphonic acid, benzenesulphonic acid or p-toluenesulphonic acid, are preferably employed. An acid which is employed in the second step of the process according to the invention is, in particular, hydrochloric acid.

In the second step of the process according to the invention, water acts simultaneously as reactant and as diluent. It is therefore employed in great excess. Between 0.5 and 5 liters, preferably between 1 and 3 liters, of water are generally used per mole of intermediate of the formula (III).

When carrying out the second step of the process according to the invention, the reaction temperatures can be varied within a substantial range. The process is generally carried out at temperatures between 20° C. and 120° C., preferably at temperatures between 50° C. and 110° C., in particular at temperatures between 80° C. and 100° C.

In a preferred embodiment of the process according to the invention, the two steps are carried out in separate batches.

To carry out the first step, the starting compound of the formula (II) is preferably dissolved in aqueous alkali metal solution, and the oxidant is then slowly metered in. The reaction mixture is stirred until the reaction has ended, and the intermediate of the formula (III) is isolated by customary methods.

For example, excess oxidant is decomposed using sodium Hydrogen sulphite, and the mixture is then acidified— for example using hydrochloric acid—and then washed using an organic solvent which is virtually immiscible with water, such as, for example, ethyl acetate. After the aqueous solution has been concentrated, the intermediate of the formula (III) is obtained in crystalline form and can be isolated by filtration.

To carry out the second step, the intermediate of the formula (III) is preferably stirred with water which contains an acid, and the mixture is heated until the reaction has ended. Working-up can be carried out in the customary manner. For example, the mixture is repeatedly extracted using an organic solvent which is virtually immiscible with water, such as, for example, methylene chloride, and the combined organic extraction solutions are dried and filtered. After the solvent has carefully been removed from the filtrate by distillation, the product of the formula (I) is obtained as the residue.

In a further preferred embodiment of the process according to the invention, both steps are carried out in a single batch, i.e. without isolation of the intermediate of the formula (III).

In this case, the triazolinethione of the formula (II) is preferably dissolved in aqueous alkali metal solution and the oxidant is then slowly metered in. The reaction mixture is stirred until the reaction has ended, excess oxidant is then destroyed, for example using sodium bisulphite, an acid, such as, for example, concentrated hydrochloric acid, is subsequently added to the reaction mixture, and the mixture is heated at the temperature required in the second step. After the reaction has ended, the mixture is worked up as described above by way of example for the second step.

The triazolinones of the formula (I) to be prepared by the process according to the invention can be used as intermediates for the preparation of agriculturally utilizable active compounds (cf. U.S. Pat. No. 3,780,052, U.S. Pat. No. 3,780,053, U.S. Pat. No. 3,780,054 and EP-A 341489).

PREPARATION EXAMPLES

Examples of the First Step

Example 1

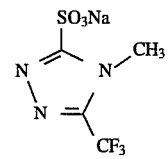

25 g (0.14 mol) of 4-methyl-5-trifluoromethyl-2,4-dihydro- 3H-1,2,4-triazole-3-thione are dissolved in 250 ml of 2.5-molar sodium hydroxide solution, and 46.5 g of a 35% strength hydrogen peroxide solution (0.48 mol of $H_2O_2$) are added in the course of 60 minutes at a reaction temperature of 40° C. to 45° C. (external cooling). The mixture is stirred for 6 hours at 40° C.; excess oxidant is then decomposed using sodium hydrogen sulphite, and the solution is acidified with 18-molar hydrochloric acid to a pH of 2. It is subsequently washed with ethyl acetate, and the aqueous solution is then concentrated under a water pump vacuum to approximately 200 ml. The solid obtained during cooling is isolated by filtration. 25 g (73% of theory) of sodium 4-methyl-5-trifluoromethyl- 4H-1,2,4-triazole-3-sulphonate are obtained.

Melting point>230° C.

$^1$H-NMR (DMSO-$D_6$, δ): 3.92 ppm.

Example 2

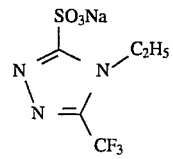

9.9 g (0.05 mol) of 4-ethyl-5-trifluoromethyl-2,4-dihydro-3H-1,2,4-triazole-3-thione are introduced into 50 ml of 2.5-molar sodium hydroxide solution. 17 ml (0.165 mol of $H_2O_2$) of a 30% strength hydrogen peroxide solution are added dropwise in the course of 20 minutes at not more than 40° C.–50° C. (cooling), stirring is continued for 6 hours at 40° C., the excess of hydrogen peroxide is destroyed by adding sodium hydrogen sulphite, and the mixture is acidified with concentrated hydrochloric acid to a pH of 2, stirred for 1 hour at room temperature and extracted repeatedly using ethyl acetate. The aqueous phase is concentrated to ⅔, and the product which has precipitated is filtered off with suction.

9.1 g (74.3% of theory) of sodium 4-ethyl-5-trifluoromethyl- 4H-1,2,4-triazole-3-sulphonate of a melting point>250° C. are obtained.

Examples of the Second Step

Example 3

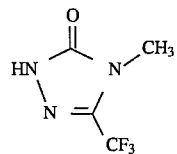

20 g (0.08 mol) of sodium 4-methyl-5-trifluoromethyl-4H-1,2,4-triazole-3-sulphonate are suspended in 200 ml of 10% strength hydrochloric acid, and the mixture is refluxed for 12 hours. This gives a clear solution which, when cold, is extracted repeatedly with dichloromethane. The combined organic extraction solutions are dried using sodium sulphate and filtered. The solvent is carefully removed from the filtrate by distillation under a water pump vacuum. 8.2 g (62% of theory) of 4-methyl-5-trifluoromethyl- 2,4-dihydro-3H-1,2,4-triazol-3-one are obtained as a solid residue of melting point 64° C.

Examples of the Complete Process

Example 4

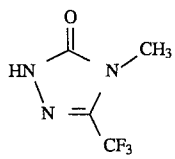

18.3 g (0.1 mol) of 4-methyl-5-trifluoromethyl-2,4-dihydro- 3H-1,2,4-triazole-3-thione are introduced into 100 ml of 2.5-molar sodium hydroxide solution. A hydrogen peroxide solution (34 ml of 30% strength hydrogen peroxide: 0.33 mol of $H_2O_2$) is slowly added dropwise at 40° C. to 50° C. and stirring of the mixture is continued for 2 hours at 50° C. Excess oxidant is then removed using sodium bisulphite, and the mixture is subsequently acidified using concentrated hydrochloric acid. The reaction mixture is then refluxed for 15 hours, subsequently stirred into ice-water and then extracted using methylene chloride. The extraction solution is dried using sodium sulphate and filtered. The solvent is carefully removed from the filtrate by distillation under a water pump vacuum. 11.3 g (68% of theory) of 4-methyl-5-trifluoromethyl- 2,4-dihydro-3H-1,2,4-triazol-3-one are obtained as a solid residue of melting point 64° C.

Example 5

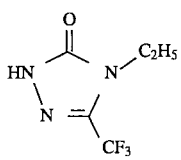

9.9 g (0.05 mol) of 4-ethyl-5-trifluoromethyl-2,4-dihydro- 3H-1,2,4-triazole-3-thione and 50 ml of 2.5-molar sodium hydroxide solution are introduced. 17 ml (0.165 mol) of 30% strength hydrogen peroxide solution are added dropwise in the course of 20 minutes at a maximum temperature of 40° C. to 50° C. (cooling), stirring is continued for 6 hours at 40° C., the excess of hydrogen peroxide is removed by adding sodium hydrogen sulphite, and the mixture is acidified using concentrated hydrochloric acid and refluxed for 10 hours. When cold, the mixture is poured into ice-water, this is extracted repeatedly using dichloromethane, the combined organic phases are dried over sodium sulphate, and the solvent is evaporated on a rotary evaporator. 5.2 g (58% of theory) of 4-ethyl-5-trifluoromethyl-2,4-dihydro-3H-1,2,4-triazol- 3-one of melting point 53° C. are obtained.

Other examples of compounds of the formula (I) which can be prepared analogously to Examples 3 to 5 are those listed in Table 1 below.

TABLE 1

Examples of the compounds of the formula (I) which can be prepared according to the invention

| Ex. No. | $R^1$ | $R^2$ | Physical Data |
|---|---|---|---|
| 6 | $CF_3$ | $CH(CH_3)_2$ | m.p.: 46° C. |
| 7 | $CHF_2$ | $C_2H_5$ | m.p.: 41° C. |
| 8 | $CF_2Cl$ | $CH_3$ | |
| 9 | $CHF_2$ | $CH_3$ | m.p.: 116° C. |
| 10 | $CF_2CHFCl$ | $CH_3$ | m.p.: 82° C. |
| 11 | $CF_2CF_3$ | $CH_3$ | m.p.: 61° C. |
| 12 | $CHF_2$ | ▷ | |
| 13 | $CF_3$ | phenyl | m.p.: 115° C. |
| 14 | $CF_3$ | $N(CH_3)_2$ | |
| 15 | $CF_3$ | $CH_2$–▷ | |
| 16 | $CF_3$ | ▷ | m.p.: 108° C. |
| 17 | $CF_3$ | $NH_2$ | m.p.: 163° C. |
| 18 | $CF_3$ | $CH_2$–▷(Cl,Cl) | m.p.: 91° C. |
| 19 | $CF_3$ | o-tolyl | |
| 20 | $CF_2CHF_2$ | $CH_3$ | m.p.: 79° C. |
| 21 | $CF_3$ | $CH_2CH=CH_2$ | $^1$H-NMR (CDCl$_3$, δ): 4.40–4.42; 4.75–4.78 ppm |
| 22 | $CF_2CF_3$ | n-$C_4H_9$ | $^1$H-NMR (CDCl$_3$, δ): 3.75–3.80; 11.75 ppm |
| 23 | $CHFCF_3$ | $CH_3$ | |
| 24 | $CH_2CF_3$ | CH3 | |
| 25 | $CF_2C_2H_5$ | $CH_3$ | |
| 26 | $CHFCH_3$ | $CH_3$ | |
| 27 | $CF_2CH_3$ | $CH_3$ | |
| 28 | $CF_2CH_3$ | $C_2H_5$ | |

Other examples of the compounds of the formula (III) which can be prepared analogously to Examples 1 and 2 are those listed in Table 2 below.

TABLE 2

Examples of the compounds of the formula (III) which can be obtained according to the invention

| Ex. No. | $R^1$ | $R^2$ | Physical Data |
|---|---|---|---|
| 29 | $CF_3$ | $CH(CH_3)_2$ | |
| 30 | $CHF_2$ | $C_2H_5$ | |
| 31 | $CF_2Cl$ | $CH_3$ | |
| 32 | $CHF_2$ | $CH_3$ | |
| 33 | $CF_2CHFCl$ | $CH_3$ | |
| 34 | $CF_2CF_3$ | $CH_3$ | |
| 35 | $CHF_2$ | ▷ | |

TABLE 2-continued

Examples of the compounds of the formula (III) which can be obtained according to the invention

| Ex. No. | R¹ | R² | Physical Data |
|---|---|---|---|
| 36 | CF₃ | 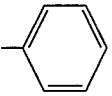 | |
| 37 | CF₃ | N(CH₃)₂ | |
| 38 | CF₃ | 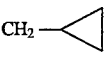 | |
| 39 | CF₃ |  | |
| 40 | CF₃ | NH₂ | |
| 41 | CF₃ | 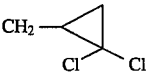 | |
| 42 | CF₃ | 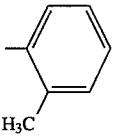 | |
| 43 | CF₂CHF₂ | CH₃ | |
| 44 | CF₃ | CH₂CH=CH₂ | |
| 45 | CF₂CF₃ | n-C₄H₉ | |
| 46 | CHFCF₃ | CH₃ | |
| 47 | CH₂CF₃ | CH₃ | |
| 48 | CF₂C₂H₅ | CH₃ | |
| 49 | CHFCH₃ | CH₃ | |
| 50 | CF₂CH₃ | CH₃ | |
| 51 | CF₂CH₃ | C₂H₅ | |

Starting Substances of the Formula (II)

Example (II-1)

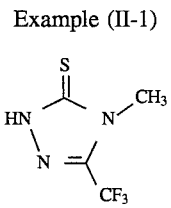

257 g (2.44 mol) of 4-methyl-thiosemicarbazide are added to 1.2 liters of trifluoroacetic acid, and the mixture is refluxed for 16 hours. It is then concentrated under a water pump vacuum, the residue is triturated with diethyl ether/ petroleum ether (5:100 by volume), and the product, which is obtained as crystals, is isolated by filtration. 444.5 g (95.5% of theory) of 4-methyl-5-trifluoromethyl- 2,4-dihydro-3H-1,2,4-triazole-3-thione of melting point 115° C. are obtained.

It will be understood that the specification and examples are illustrative but not limitative of the present invention and that other embodiments within the spirit and scope of the invention will suggest themselves to those skilled in the art.

What is claimed is:

1. A process for preparing a triazolinone of the formula

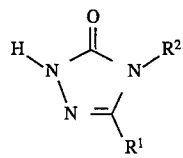

in which

R¹ represents alkyl having 1 to 6 carbon atoms which is optionally substituted by halogen, cyano or C₁-C₄-alkoxy, or represents cycloalkyl having 3 to 6 carbon atoms which is optionally substituted by halogen, cyano or C₁-C₄-alkyl, and R² represents amino, a radical selected from the group consisting of alkyl, alkenyl, alkinyl, alkoxy, alkylamino or dialkylamino, each of which has up to 6 carbon atoms in the alkyl, alkenyl or alkinyl groups and each of which is optionally substituted by halogen, cyano or C₁-C₄-alkoxy, or represents a radical selected from the group consisting of C₃-C₆-cycloalkyl, C₃-C₆-cycloalkyl-C₁-C₂-alkyl or phenyl, each of which is optionally substituted by halogen, cyano, C₁-C₄-alkyl, C₁-C₄-alkoxy or C₁-C₄-alkoxycarbonyl which comprises 1) reacting a triazolinethione of the formula

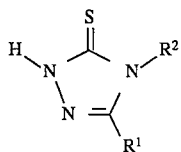

with an oxidant at a temperature range between 0° and 100° C., optionally in the presence of a reaction auxiliary and a solvent; followed by 2) taking the triazolesulphonic acid

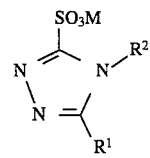

wherein

M represents hydrogen or a metal equivalent, formed in step 1 above and reacting said compound with water at a temperature range of 20° C. and 120° C. optionally in the presence of an acid, wherein the oxidant is selected from the group consisting of oxygen, ozone, hydrogen peroxide, chlorine, sodium hypochlorite solution, sodium permanganate, potassium permanganate, nitric acid, sodium dichromate, potassium dichromate, sodium peroxodisulphate, potassium peroxodisulphate, sodium perborate, potassium perborate, performic acid, peracetic acid, perpropionic acid and optionally halogenated perbenzoic acids, and the reaction auxilary is salt of a metal of groups IVb, Vb and VIb or a inorganic or organic base.

2. A process for the preparation of a triazolinone according to claim 1, wherein R¹ represents methyl, ethyl, n- or i-propyl, or n-, i- or s-butyl, each of which is optionally substituted by fluorine, chlorine, bromine, cyano, methoxy or ethoxy, or represents cyclopropyl, cyclopropylmethyl, cyclobutyl, cyclopentyl or cyclohexyl, each of which is optionally substituted by fluorine, chlorine, bromine, cyano or methyl, and R² represents amino, a radical selected from the group consisting of methyl, ethyl, n- or i-propyl, n-, i- or s-butyl, allyl, propargyl, methoxy, ethoxy, n- or i-propoxy, n-, i- or s-butoxy, methylamino, ethylamino, n- or i-propylamino, n-, i- or s-butylamino, dimethylamino or diethylamino, each of which is optionally substituted by fluorine, chlorine, cyano, methoxy or ethoxy, or represents a radical selected from the group consisting of cyclopropyl, cyclobutyl, cyclopentyl or cyclohexyl or phenyl, each of which is optionally substituted by fluorine, chlorine, bromine, cyano, methyl, ethyl, n- or i-propyl, methoxycarbonyl or ethoxycarbonyl.

3. A process for the preparation of a triazolinone according to claim 1, wherein R¹ represents methyl, ethyl, n- or i-propyl, cyclopropyl or cyclopropylmethyl, each of which is mono-, di-, tri-, tetra-, penta-, hexa- or heptasubstituted by fluorine and/or chlorine and R² represents methyl, ethyl, n- or i-propyl, methoxy, ethoxy, methylamino, ethylamino, dimethylamino, cyclopropyl, phenyl or tolyl.

4. A process according to claim 1, wherein the reaction is carried out at temperatures between 20° C. and 80° C. in the first phase of the process and at temperatures between 50° C. and 110° C. in the second phase of the process.

5. A process according to claim 1, wherein in the reaction in the first phase of the process, between 3 and 4 mole of an oxidant are employed per mole of triazolinethione of the formula

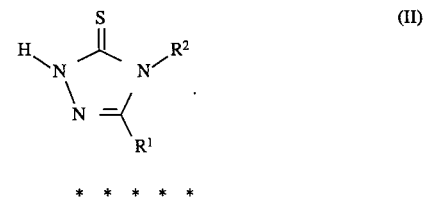

(II)

* * * * *